United States Patent [19]
Froehler et al.

[11] Patent Number: 5,164,491
[45] Date of Patent: Nov. 17, 1992

[54] LARGE SCALE SYNTHESIS OF OLIGONUCLEOTIDES AND THEIR ASSOCIATED ANALOGS

[75] Inventors: Brian C. Froehler, Belmont; Kenneth M. Kent, Mt. View; Sylvia Wu, Castro Valley, all of Calif.

[73] Assignee: Gilead Sciences, Foster City, Calif.

[21] Appl. No.: 366,849

[22] Filed: Jun. 15, 1989

[51] Int. Cl.$^5$ .......................................... C07H 17/00
[52] U.S. Cl. ................................................ 536/27
[58] Field of Search .................................... 536/27

[56] References Cited

U.S. PATENT DOCUMENTS 4,415,732 11/1983 Caruthers et al. .................. 536/27
4,458,066 7/1984 Caruthers et al. .................. 536/27

FOREIGN PATENT DOCUMENTS

0155950 B1 10/1985 European Pat. Off. .
0219342 A2 4/1987 European Pat. Off. .

OTHER PUBLICATIONS

Chow et al., Nucl. Acids Res., 1982, 9(12):2807-2817.
Froehler and Matteucci, Nucl. Acids Res., 1983, 11(22):8031-8036.
Froehler, Tetrahedron Lett., 1986, 27(46):5575-5578.
Froehler and Matteucci, Tetrahedron Lett., 1986, 27(4):469-472.
Froehler et al., Nucl. Acids Res., 1986, 14(13):5399-5407.
Froehler and Matteucci, 1987, Nucleosides & Nucleotides, 6(1&2):287-291.
Froehler et al., Nucl. Acids Res., 1988, 16(11):4831-4839.
Letsinger and Mahadevan, J. Am. Chem. Soc., 1966, 88(22):5319-5324.
Letsinger et al., Biochemistry, 1967, 6(5):1379-1387.
Lyttle et al., BioPharm., 1988, Jul./Aug.:34-38.
Marugg et al., Tetrahedron Lett., 1986, 27(23):2661-2664.
Matsukura et al., Proc. Natl. Acad. Sci. USA, 1987, 84:7706-7710.
Melby and Strobach, J. Am. Chem. Soc., 1967, 89(20):450-453.
Melby and Strobach, J. Org. Chem., 1969, 34(2):421-427.
Melby and Strobach, J. Org. Chem., 1969, 34(2):427-431.
Mitchell et al., J. Org. Chem., 1978, 43(14):2845-2852.
Moser and Dervan, Science, 1987, 238:645-650.
Sherman et al., Science, 1985, 230:412-417.

Primary Examiner—John W. Rollins

[57] ABSTRACT

The present invention describes methods for the production of oligonucleotides under conditions which exploit the desirable characteristics, such as the property of sustaining high degrees of substitution, of functionalized organic polymeric supports while avoiding the sluggish kinetics and low rates of conversion which normally plague syntheses involving such solid supports. By employing the methods and materials disclosed, functionalized support, substituted to a degree of about 250 μmol/g, can be utilized at greater than 98% conversion levels for each sequential nucleotide coupling cycle, to provide unprecedented amounts of isolated oligonucleotide per gram of solid support.

14 Claims, 2 Drawing Sheets

LARGE SCALE SYNTHESIS OF OLIGONUCLEOTIDES AND THEIR ASSOCIATED ANALOGS

1. INTRODUCTION

The present invention describes methods for the efficient synthesis of oligonucleotides of variable length, as well as their associated analogs, The materials and methods disclosed herein provide a unique procedure by which a high degree of substitution on the solid support may be achieved, while observing high conversions of the reactants present and isolating high yields of the desired end-products. These characteristics, along with the surprising ability to recover valuable excess reagent monomers, combine to give a convenient and highly cost effective means for the production of nucleic acid fragments. In addition, novel monomethoxytritylated nucleoside H-phosphonate compounds are disclosed which are useful reagents for the high efficiency synthesis of polynucleotides.

2. BACKGROUND OF THE INVENTION

2.1. Synthetic Oligonucleotides and Their Utility

Oligonucleotides and, in particluar, oligodeoxynucleotides (DNA) enjoy a special status among the tools used by the scientific biological community. In its pursuit of knowledge regarding the intimate workings and details of the body's mechanism for expressing particular traits and the development of certain abnormalities and mammalian disease, sequence-specific oligonucleotides have been used in recombinant host-vector systems and, in diagnostic assays, as intermediates in the preparation of labeled oligonucleotide probes. DNA fragments of a few to tens of bases in length are useful models for the study of the local interaction of DNA with foreign agents or known therapeutic compounds (See, for example, Lippard et al. in *Science* 1985, 230, 412).

Recently, oligodeoxynucleotides, which are complementary to certain gene messager RNA or viral sequences, have been reported to inhibit the spread of disease related to viral and retroviral infectious agents (See, for example, Matsukura et al. in *Proc. Natl. Acad. Sci. USA* 1987, 84, 7706, and references cited therein). It has also been reported that oligonucleotides can bind to duplex DNA via triple helix formation and, presumably, inhibit transcription and/or DNA synthesis (See, Moser and Dervan in *Science* 1987, 238, 645).

These oligonucleotides are referred to as "antisense" compounds, and they, themselves, represent a whole class of therapeutic agents which exhibit antiviral activity and/or inhibit viral DNA synthesis or protein synthesis. Moreover, analogs of DNA having internucleotide phosphate linkages different from the phosphate diester groups of normal DNA have been found to possess their own unique characteristics which are desirable in certain applications. For example, methyl phosphonate analogs of DNA, perhaps being uncharged, demonstrate greater hydrophobicity and readily pass through cell membranes while inhibiting protein synthesis. The thiophosphate analogs are more resistant to degradation by nucleosides than their phosphate diester counterparts and are thus expected to have a higher persistence in vivo and greater potency. Phosphoramidate derivatives of oligonucleotides are known to bind to complementary polynucleotides and have the additional capability of accommodating covalently attached ligand species (See, for example, Froehler et al. in *Nucleic Acids Res.* 1988, 16(11), 4831).

Thus, oligonucleotides and their associated analogs have a well-established utility in biological and chemical research, but their synthesis is invariably time consuming, tedious, and costly.

2.2. Preparative Methods

Since the pioneering work by Merrifield and coworkers in the area of solid phase-supported synthesis of polypeptides, the preparation of synthetic "biological" polymers under heterogeneous conditions has been pursued with keen interest by research workers in many laboratories. Of particular and present interest in the fields of molecular biology and biological chemistry is the development of a practical in vitro synthesis of DNA, RNA, or their associated analogs and derivatives. Among the earliest work in the area of solid phase-supported synthesis of oligonucleotides was that of Lestinger and co-workers (See, e.g., *J. Am. Chem. Soc.* 1966, 88(22), 5319) who described the use of "popcorn" copolymers prepared from styrene, p-vinylbenzoic acid, and p-divinylbenzene. These copolymers were found to be insoluble in water, alkaline solutions, and "all organic solvents examined" (Ibid, at page 5320, col. 1). The condensation chemistries described in these references involve multiple steps including the phosphorylation of polymer bound nucleoside followed by coupling of the phosphoryl derivative with an added nucleoside. The protocols associated with this, and similar techniques, required reaction times in the order of days but disclosed the use of a variety of sugar hydroxyl protecting groups including trityl, monomethoxytrityl, and dimethoxytrityl moieties (See, e.g., *Biochemistry* 1967, 6(5), 1379).

Thereafter, other derivatives of styrene polymers were developed as the insoluble polymer support. Of note were the tritylated polymers described by Melby and Strobach (See, e.g., *J. Am. Chem. Soc.* 1967, 89(2), 450). The solvent in popular use for the condensation reactions described in the foregoing references was pyridine, but certain solubility problems persisted, especially with particular acylated nucleosides as starting materials (See, e.g., *J. Org. Chem.* 1969, 34(2), 427). Although fairly high loading of initial nucleosides were possible, the degress of conversion remained very low and were, in fact, inversely proportional to the degree of loading. Other solvents, such as methylene chloride, dioxane, and dimethylformamide were described as either "unsuitable" or provided "diminished conversions" (See, e.g., *J. Org. Chem.* 1969, 34(2), on page 423).

More recently, Merrifield and co-workers described, in *J. Org. Chem.* 1978, 43(14), 2845, yet another derivatized styrene polymer, an aminomethylated resin, useful in the preparation of a 4-(oxymethyl)-phenylacetamidomethylpoly(styrene-co-divinylbenzene), the preferred solid support for polypeptide syntheses. Nevertheless, the drawbacks associated with organic polymeric solid supports, which have led research workers in the field to abandon them in favor of inorganic supports, are perhaps best summarized in U.S. Pat. No. 4,415,732, issued Nov. 15, 1983 to Caruthers and Beaucage which states, in part, that "prior art polymers used in such synthesis have proven inadequate for reasons such as: (1) slow diffusion rates of activated nucleotides into the support; (2) excessive swelling of various macroporous, low cross-linked support polymers; and (3) irreversible absorption of reagent onto the polymer" (col. 1, lines 34-40). Caruthers and Beaucage also describe in this patent the utility of phosphoramidite compounds as intermediates in the preparation of polynucleotides and prefer, as most researchers do at present, inorganic solid supports derived from silica gel or controlled pore glass (CPG).

Indeed, the functionalization of silica support is discussed by Chow et al. in *Nucleic Acids Res.* 1982, 9(12), 2807, along with the use of 5'-dimethoxytritylnucleoside 3'-O-methylphosphochloridites as reagent monomers in the synthesis of oligonucleotides. Froehler and co-workers have recently described oligonucleotide synthetic methods which are carried out on inorganic supports (See, for example, *Tetrahedron Lett.* 1986, 27(4), 469 and *Nucleic Acids Res.* 1986, 14(13), 5399). In these references, Froehler et al. discuss the particular advantages associated with the use of nucleoside H-phosphonate derivatives in the preparation of polynucleotides and certain internucleotide phosphate-linked analogs (See, also, *Tetrahedron Lett.* 1986, 27(46), 5575). In European Patent Application 0 219 342, Froehler and Matteucci describe a process for the synthesis of polynucleotides which involves the sequential addition of 5'-dimethoxytrityl-3'-nucleoside H-phosphonates to deprotected nucleoside derivatives bound to an insoluble carrier. As before, the preferred carrier is controlled pore glass, although the published application states that "silica gel or polystyrene also are acceptable" (page 3, line 14). Despite this statement, the teachings of this reference are not generally applicable to organic polymer supports. In fact, the reaction conditions under which many of the synthetic steps outlined in this European Patent Application are well-suited only for syntheses carried out on inorganic solid supports.

The automation of DNA synthesis is an area which is actively being pursued by commercial instrument manufacturers. In an article which appeared in *BioPharm* 1988, July/August, 34, Lyttle et al. summarize the merits of large-scale automated synthesis under heterogeneous conditions. Again, the preferred solid support is CPG. As in the references discussed above, involving the early work with organic polymer supports, there is no disclosure, indeed no recognition, in this or any of the preceding references, concerned with the use of inorganic supports, of the striking results made possible by the discoveries of the present invention.

Thus, the current state of the art, reveals existing procedures which are still immensely expensive, inherently wasteful, and which leave the prospect for an economical large scale synthesis of oligonucleotides, or associated analogs and derivatives thereof, lying prohibitively beyond tolerable cost considerations. Indeed, in a recent article, which appeared in *The Wall Street Journal* 1989, June 8, B7, describing the promising developments in the treatment of patients afflicted with autoimmune disorder syndrome (AIDS), and in particular, the use of antisense compounds, Dr. Samuel Broder, current director of the National Cancer Institute, is quoted as stating that the human testing of such antisense "particles" would not begin for another year or two, in part, because of the need for scientists to overcome the technical problem of scaling up "production of anti-sense particles 'from the milligram to the kilogram level'" Dr. Broder adds that such a large scale synthesis "is a challenge for a field that only two years ago 'would have been labeled science fiction.'"

3. SUMMARY OF THE INVENTION

The present invention discloses methods for the economical large scale synthesis of oligonucleotides or their associated analogs and derivatives which take advantage of the swellable characteristics of organic polymer supports without encountering the associated difficulties which have been extensively described by others. The heterogeneous conditions employed in the present invention involve a solvent system which is capable of swelling the organic polymer support, thus maximizing the number of available reactive sites participating at each condensation cycle, and which solvent system, when used in conjunction with a suitable activating agent, is also able to promote the condensation reaction to a degree effective to provide efficient coupling for each condensation.

The present invention also discloses novel monomethoxytrityl-protected nucleoside H-phosphonates which, along with the other aspects of the invention, enable the oxidation, cleavage, and isolation of the product oligonucleotides in amounts which are unprecedented based on the amount of solid support employed. Additional disclosures of the invention describe modifications to existing instrumentation which allow for the automated production of oligonucleotides in millimolar amounts per run and which also permit the recovery of valuable reagent monomers in a form which is suitable for subsequent preparative runs.

Thus, it is an object of the present invention to provide a synthetic procedure which provides a high degree of subsitution per gram of functionalized solid support while maintaining high levels of conversion with each coupling cycle.

It is also an object of the present invention to provide such a high efficiency process which enables the economical production of up to millimolar quantities of oligonucleotides in a single run.

Yet another object of the instant invention is to provide a method for forming an internucleotide H-phosphonate bond under conditions which promote the participation of the greatest number of available nucleoside groups and with the most favorable rates of reaction.

Accordingly, one embodiment of the present invention involves a method of forming an internucleotide H-phosphonate linkage which comprises:

(a) providing a first nucleoside compound having terminal 5'-hydroxyl and 3'-hydroxyl ends, one of which ends is bound to a swellable organic polymeric support and the other end remaining unbound;

(b) allowing a second nucleoside compound having terminal 5'-hydroxyl and 3'-hydroxyl ends, one of which ends is blocked by a hydroxyl protecting group and the other bearing a H-phosphonate group, to undergo a condensation reaction with said first nucleoside compound having said end remaining unbound, said condensation reaction being allowed to take place in the presence of a suitable dehydrating agent and in a solvent system capable of: (i) swelling said support, and (ii) promoting said condensation reaction, for a sufficient period of time to form a polymer-bound oligonucleotide having an internucleotide H-phosphonate linkage and having terminal 5'-hydroxyl and 3'-hydroxyl ends, one of which ends is blocked by a hydroxyl protecting group.

Yet another embodiment of the present invention involves a process for the synthesis of a protected oligonucleotide, or analog thereof, having terminal 5'-hydroxyl and 3'-hydroxyl ends, one of which ends is blocked by a suitable protecting group which comprises:

(a) providing a first nucleoside compound having terminal 5'-hydroxyl and 3'-hydroxyl ends, one of which ends is bound to a swellable organic polymeric support and the other end remaining unbound;

(b) allowing a second nucleoside compound having terminal 5'-hydroxyl and 3'hydroxyl ends, one of which ends is blocked by a hydroxyl protecting group and the other bearing a H-phosphonate group, to undergo a condensation reaction with said first nucleoside compound having said end remaining unbound, said condensation reaction being allowed to take place in the presence of a suitable dehydrating agent and in a solvent system capable of: (i) swelling said support; and (ii) promoting said condensation reaction;

(c) removing said hydroxyl protecting group from said blocked end of said second nucleoside compound which had undergone said condensation reaction of step (b);

(d) repeating steps (b) and (c) in sequence using preselected nucleoside compounds until the penultimate nucleoside of the desired sequence structure is in place;

(e) allowing a terminal nucleoside compound having terminal 5'-hydroxyl and 3'-hydroxyl ends, one of which ends is blocked by a suitable protecting group and the other bearing a H-phosphonate group, to undergo a condensation reaction with said penultimate nucleoside, to provide a polymer-bound intermediate oligonucleotide H-phosphonate;

(f) oxidizing said polymer-bound intermediate oligonucleotide H-phosphonate to the corresponding polymer-bound protected oligonucleotide, or analog thereof; and (g) cleaving said polymer-bound protected oligonucleotide, or analog thereof, from said swellable organic polymeric support, to provide a protected oligonucleotide, or analog thereof, having terminal 5'-hydroxyl and 3'-hydroxyl ends, one of which ends is blocked by a suitable protecting group.

Another important object of the present invention relates to providing processes which minimize the amounts of reagents or reactants used with each coupling or condensation step and, thus, reducing the costs associated with each process overall.

A further object of the present invention is to provide a novel set of reagent monomers and allow for a means for recovering any excess amounts thereof which may remain after each coupling cycle.

Other objects of this invention will become apparent to those skilled in the art after considering the following and additional descriptions and examples.

5 DETAILED DESCRIPTION OF THE INVENTION

5.1. Functionalized Solid Support

Figure 1:
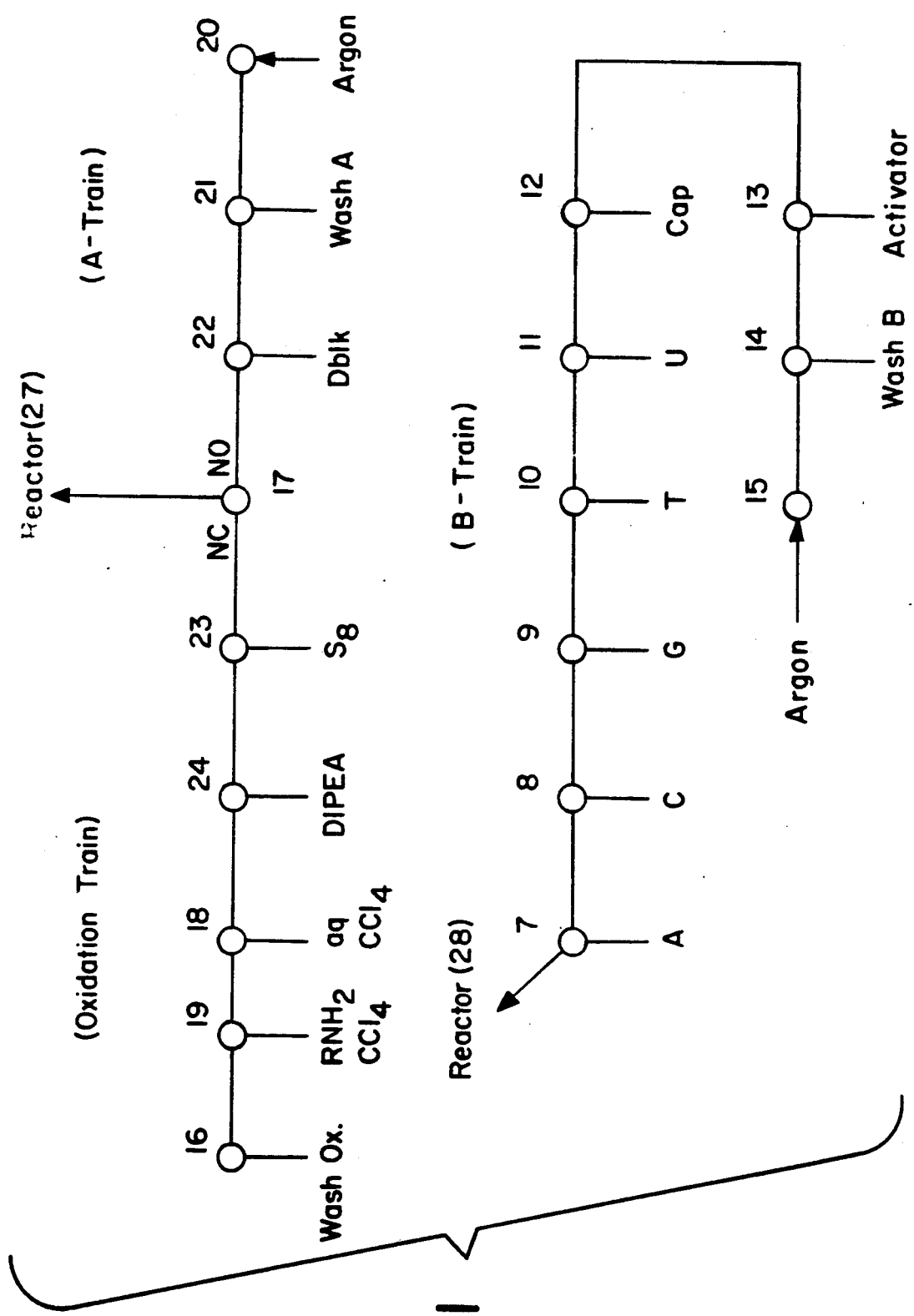
FIG. 1 is a schematic flow diagram for the "A," "B" and "Oxidation" Trains of an automated, microprocessor controlled reactor system useful for the large scale synthesis of oligonucleotides.

The term "functionalized" as used in the present invention means the condition or state in which desirable molecular entities are covalently bound to the backbone of a suitable solid polymer support. In the present invention, such molecular entities comprise the initial nucleoside residue which forms one end of the oligonucleotide and which serves as the anchor to which is attached successive base residues of the growing chain. After exposure of the functionalized solid support to several coupling or condensation cycles, as described in more detail below, the covalently bound nucleosides may be treated, under the appropriate reaction conditions, with reagents which cleave and release the end product from the solid support.

Accordingly, the solid support employed in the instant invention is a solvent swellable polymeric material which contains reactive functional groups which may be further modified to include the desired nucleosides. An example of a suitable polymer is polystyrene which has been derivatized to include a reactive functional group such as aminomethyl, hydroxymethyl, or carboxymethyl substituted for the hydrogen at the 4-position of the styrene phenyl groups. Other types of swellable polymers may also be useful including, but not limited to, poly(dimethylacrylamide-co-ethylenebisacrylamide), poly(styrene-co-butadiene), and poly(acryloylmorpholide).

In a particular embodiment of the present invention, the preferred polymeric solid support is an aminomethylated resin derived from poly(styrene-co-divinylbenzene). The most preferred derivatized solid support is the copolymer having 1% divinylbenzene prepared, for example, by the method described by Merrifield and co-workers in *J. Org. Chem.* 1978, 43, 2845, the complete disclosure of which is incorporated herein by reference.

As mentioned briefly above, the choice of solvent, or solvent mixture, is critical to the practice of the present invention. Nevertheless, a wide variety of solvents may be employed so long as the solvent system finally chosen fulfills at least two key requirements: namely, (i) that the solvent system is capable of swelling the organic polymeric support; and (ii) that it is compatible with and promotes the reaction chemistry of the condensation step. For example, a solvent such as acetonitrile is compatible with the reaction chemistry of H-phosphonates and is able to promote the coupling reaction. Overall, however, acetonitrile is not a suitable solvent because it shrinks, not swells, styrene polymers. By a similar token, certain dipolar aprotic solvents like DMF slow down the condensation reaction and are, therefore, least preferred. In general, however, aromatic solvents, halogenated solvents, and certain slightly polar solvents are useful in the present invention. More particularly, solvents such as pyridine, benzene, toluene, methylene chloride, chloroform, trichloroethane, and the like are preferred solvents. Other solvents such as dioxane, tetrahydrofuran, N-methylpyrrolidone, and dimethylacetamide are also of some benefit. The use of oxidizing solvents such as carbon tetrachloride or carbon tertrabromide should be limited, however, to the steps involving oxidation of the oilgonucleotide H-phosphonate. Solvent mixtures comprising mixtures of chlorinated solvents or mixtures of chlorinated and non-chlorinated solvents may also be employed to good advantage.

In the present invention, a high degree of functional group substitution is achieved which is exploited successfully to provide high yields in a large scale synthesis of oligonucleotides. By employing the methods of the present invention, typical loading levels of the initial base residue on the solid support can range from about 100 μmol of bound nucleoside per gram of functionalized (substituted) support to over about 1000 μmol/g. It is understood, of course, that the degree of substitution may be tailored to the particular application at hand. Generally, however, the degree of substitution ranges from about 200 to about 600 μmol/g.

Thus, in one embodiment of the present invention, an aminomethylated poly(styrene-co-(1%)divinylbenzene) is functionalized by combining the solid support with a protected nucleoside-3,-succinate ester in a suitable solvent mixture. Preferably, the functionalization process is carried out in the presence of a base and an effective amount of an agent, such as a carbodiimide, which promotes the formation of amide linkages. As mentioned previously, the degree of substitution may be varied according to individual needs. Such variation may be achieved, for example, by adjusting the amount of the initial reagent nucleoside relative to the amount of solid support or by adjusting the reaction time. The loading level may be monitored conveniently via a spectrophotometric method described further in Section 6.2, infra.

Scheme I illustrates the functionalization process including the "capping" step to deactivate any free unfunctionalized amino groups on the solid support.

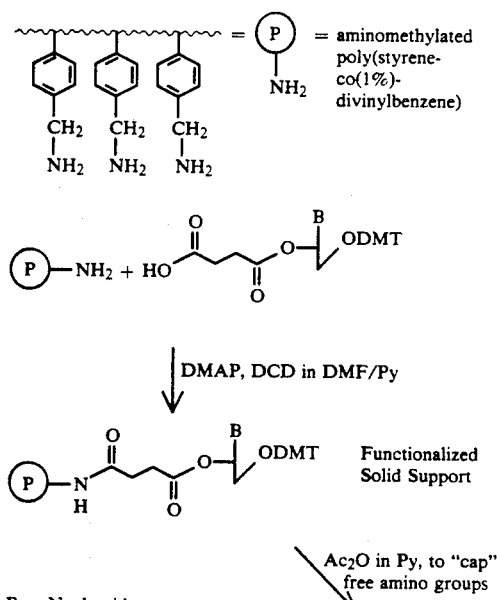

Scheme I

B = Nucleoside
DMT = Dimethoxytrityl
DMAP = N,N-Dimethylaminopyridine
DCD = Diisopropylcarbodiimide
Ac₂O = Acetic Anhydride
DMF = N,N-Dimethylformamide
Py = Pyridine

5.2. Synthesis of Oligonucleotide H-Phosphonates

Employing the functionalized solid support, whose preparation and degree of substitution is governed by the procedure described in the preceding Section, one may initiate the large scale synthesis of nucleoside H-phosphonate oligomers. It should be pointed out that the methods of the present invention may be performed manually with equal efficacy. In order to realize the maximum benefits of ease, convenience, and economy, however, the procedures outlined herein are preferably carried out with the aid of a microprocessor controlled automatic DNA synthesizer. Such instruments have undergone intense periods of development and are available currently from a number of commercial sources, including Milligen/Biosearch, Inc. (Navato, Calif., USA), Applied Biosystems, Inc. (Foster City, Calif., USA), and DuPont Co. (Wilmington, Del., USA). Furthermore, these instruments may be modified to incorporate additional features which may be of particular interest to the individual scientist. Such a customized modification is discussed further below.

5.2.1. Suggested Modification of a Commercial Automated DNA Synthesizer

As described briefly above, the methods of the present invention are preferably practiced with the aid of a microprocessor controlled DNA synthesizer. Using an instrument manufactured by Biosearch, Inc., Model 8800, the following general descriptions and alterations may be applied to provide an automated system compatible with the methods disclosed herein. A generalized description of this particular instrument, including instrument control system, may be found in an article by Lyttle and co-workers, in *BioPharm* 1988, July/August, 34, the complete disclosure of which is incorporated herein by reference.

Referring now to FIG. 1, the monomers, reagents, oxidizing solutions, wash solutions, and others are divided into three "trains" labeled "Oxidation," "A," and "B," as shown. The protected nucleoside H-phosphonate monomers at 7, 8, 9, 10 and 11 and the ethyl H-phosphonate "capping" reagent at 12 are most conveniently situated in the B-Train. Wash solution B, containing pyridine at 14 and the activating agent at 13 are also present in the B-Train. The Oxidation Train is equipped with the reagents shown in FIG. 1, while the A-Train is delegated to deblocking solution at 22 and wash solution A (methylene chloride) at 21, as well as an inert gas line 20 (also present in at 15 of the B-Train). The acronyms "NC" and "NO" mean "normally closed" and "normally open," respectively.

Figure 2:
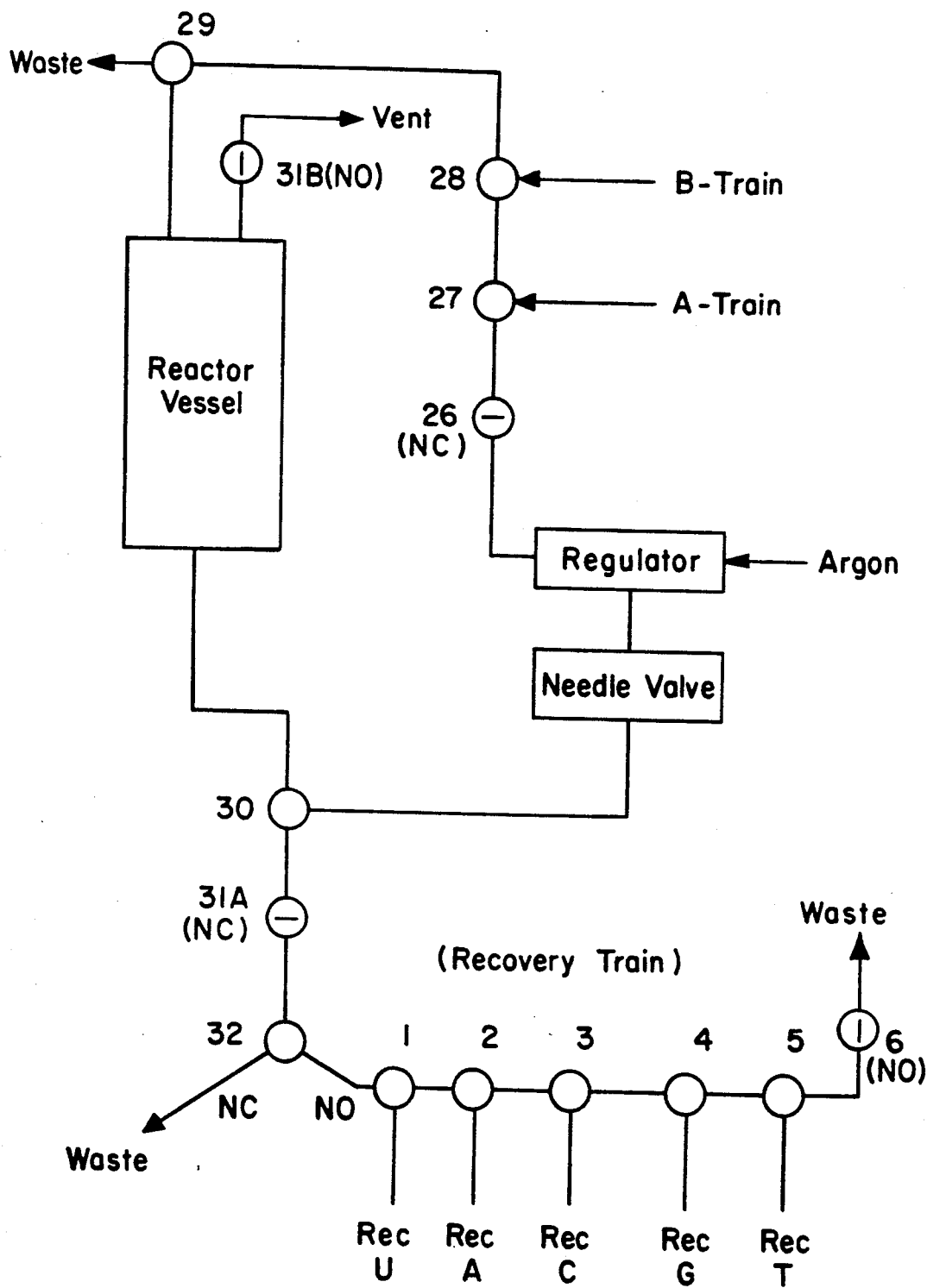
FIG. 2 is a schematic flow diagram further outlining a possible configuration of the "Recovery" Train relative to the reactor vessel of an automated system for the recovery of excess reagent monomers and the large scale synthesis of oligonucleotides.

Certainly, the most important modification to the existing instrumentation is the installation of the Recovery Train which is illustrated as part of FIG. 2. In the present apparatus, at total of six outputs, 1-6, are placed in line as shown: five assigned to nucleoside reagents and a sixth for waste. The microprocessor does most of the work, actuating valves and diverting spent solutions to particular recovery vessels.

5 2 2. Conditioning of the Solid Support and Initiation of the Condensation Cycles Virtually any desired oligonucleotide sequence may be prepared economically and efficiently by the methods of the present invention. Beginning with the initial nucleoside used to functionalize the solid support, and which nucleoside forms the first base residue at the 3'-end of the contemplated oligonucleotide, successive monomer units are attached to the growing chain with unprecedented effectiveness and at the high substitution levels made possible by the use of the swellable organic polymeric solid support and corresponding reaction solvent systems herein described. It is understood that while the present discussion focuses on the procedure in which the oligonucleotide chain is lengthened via the free or unbound 5'-hydroxyl end, an appropriate procedure may also be devised, employing appropriate reagents, in which the oligonucleotide is bound to the support by its 5'-end and chain growth takes place through condensation reactions involving the 3'-end.

Initially, the functionalized solid support is swollen with an appropriate solvent, such as dichloromethane, and subjected to several cycles involving exposure to this solvent, agitation, purging the solvent off, and reexposure. These wash steps may involve one or more types of solvent and are undertaken to help ensure that impurities, unused or excess reactants, and other reagents are removed prior to the start of a new round of coupling or condensation reaction. After the solid support is swollen and washed several times, the 5'-hydroxy protecting group of the nucleoside sugar moiety is removed by the introduction of acidic media. The solid support is then washed with fresh amounts of dichloromethane, followed by a basic solvent (e.g., pyridine). The unprotected 5'-hydroxyl group of the bound nucleoside is then ready for exposure to a slight excess of a preselected reagent monomer bearing an H-phosphonate group at the 3'-position of the sugar moiety and a protecting group at the 5'-end.

In the present invention, the condensation reaction is promoted by the presence of a suitable dehydrating agent. The dehydrating agent or "activator" may be selected from a number of compounds which are well recognized in the art as promoting the formation of a sugar hydroxyl/H-phosphonate bond. Some dehydrating agents suitable for use in the present invention include, but are not limited to, phosphorylating agents or acylating agents, such as isobutyl chloroformate, diphenyl chlorophosphate, acid anhydrides, or acid halides, such as 1-adamantane carboxylic acid chloride. The preferred dehydrating agent is a pivaloyl halide, most preferably pivaloyl chloride. In the present invention, it has been discovered quite unexpectedly that the coupling reaction works considerably better when the amount of pivaloyl chloride used corresponds to about 1 equivalent (equiv) or less, of the amount of nucleoside monomer added to the solution. This discovery contrasts quite remarkably with the prevailing impression in the art that a large excess (about 5 equiv) of the dehydrating agent is needed to effect a smooth coupling.

The condensation reaction described above is carried out in a solvent system which is capable of swelling the organic polymeric support and, also, promoting the reaction. Preferably, such a solvent system comprises a polyhalogenated solvent and a basic aromatic solvent. Most preferably, the solvent system comprises an anhydrous mixture of pyridine, dichloromethane, and a suitable sterically hindered base. Examples of a suitable sterically hindered base include, but are not limited to, diisopropylethylamine, 2,4,6-collidine, and 2,6-lutidine, the latter being preferred. Significantly, the discovery that the condensation reaction proceeds smoothly with only a small amount of activator allows the addition of the sterically hindered base to the solvent system. The presence of the added base, in turn, encourages the coupling reaction to proceed more effectively (i.e., with better conversion and a faster rate) relative to a reaction which contains only pyridine as the basic component. Consequently, and of equal importance, such favorable conditions for coupling dispenses with the need for a very large excess of precious reagent monomer during each coupling cycle. Indeed, the amount of reagent monomer compound (which may be a monomer or an oligomer) used in the present methods is quite low, typically about 1.5 equiv of solubilized monomer per polymer-bound nucleoside or polynucleoside H-phosphonate. It should be noted that the presence of a base stronger than, for example, pyridine would have led to a highly undesirable modification of the synthetic oligonucleoside H-phosphonate backbone under the reaction conditions of the prevailing art which specify the need for a large excess, at least about 5 equiv, of dehydrating agent during the coupling cycle. In particular, the strong base and excess activator can lead to the conversion of the H-phosphonate internucleotide linkages to alpha-keto phosphonates derived from the activator molecules. (See, for example, Froehler and Matteucci in *Nucleosides and Nucleotides* 1987, 6, 287)

After the condensation reaction has been allowed to proceed for a sufficient amount of time, the spent reagent solution from the coupling reaction is then purged from the reactor and set aside as described further, below. Subsequently, the solid support is subjected to prescribed wash cycles and, preferably, exposed to another pass of fresh reagent monomer solution as detailed in Section 6.3, infra. This double exposure of the functionalized solid support to the reagent monomer solution is sufficient, in most cases, to ensure the participation of at least about 99% of the available 5'-hydroxyl groups. Also, while a separate "capping" step is ordinarily not necessary to deactivate the very small number of 5'-hydroxyl groups which may remain unreacted, the present invention retains the flexibility of accommodating such a step, if desired. Such a separate "capping" step is best accomplished by the addition of a solution of a dehydrating agent and ethyl H-phosphonate, a smaller and kinetically more favored reagent for engaging these residual 5'-hydroxyl groups.

As described in the Examples Section of this disclosure, the coupling cycle is then performed for each succeeding member of the desired oligonucleotide H-phosphonate sequence until the sequence is complete. Preferably, the coupling cycles are carried out until the penultimate base residue is in place. Thereafter, the last member of the chain is introduced under conditions similar to the preceding reagent monomers except that the 5'-hydroxyl blocking group employed in the nucleoside compound comprises one which is capable of affording superior protection for the 5'-OH group. Keeping in mind that the subsequent steps in the synthesis involve the oxidation of the DNA H-phosphonate, followed by cleavage of the oligonucleotide from the solid support, and finally, isolation and purification steps, it is highly desirable, if not imperative, that such a suitable protecting group survive these potentially harsh reaction conditions. It should be noted that such a suitable protecting group may also assist in the subsequent purification steps. For example, a particular aliphatic or aromatic acyl group may provide characteristics which allow for an easier chromatographic separation. Such protecting groups may even be a proteinaceous substance, such as biotin, for exploiting an affinity column containing avidin. Furthermore, various hydrophilic or hydrophobic groups may also be utilized depending on the contemplated purification scheme. Still other methods and materials may be useful which are apparent to those skilled in the art.

In a particular embodiment of the present invention, it has been demonstrated that a protecting group based on the monomethoxytrityl cation affords the improved stability needed to achieve a superior isolated yield of end product after the oxidation and cleavage steps. Moreover, the monomethoxytrityl group is also able to provide the desirable chromatographic characteristics which enable one to distinguish, separate, and purify the oligomer molecules which incorporate the full complement of desired base residues from those "failed" sequences which lack the entire sequence (See, for example, Section 6.6). Thus, in one aspect of the present invention, new compositions of matter are disclosed which are useful in the synthesis of oligonucleotides and which have the important characteristics described supra. These novel compounds are the monomethoxytritylnucleoside H-phosphonates: 5'-monomethoxytritylthymidine 3'-H-phosphonate, 5'-monomethoxytrityl-$N^6$-benzoyldeoxyadenosine 3'-H-phosphonate, 5'-monomethoxytrityl-$N^4$-benzoyldeoxycytidine 3'-H-phosphonate, 5'-monomethoxytrityl-$N^2$-isobutyryl-deoxyguanosin 3'-H-phosphonate, 5'-monomethoxytrityl-$N^4$-benzoyldeoxy-5-methylcytidine 3'-H-phosphonate, 5'-monomethoxytrityl-5-bromouridine 3'-H-phosphonate, derivatives, and analogs thereof.

It is understood, of course, that in view of the procedure described in Section 6.9 for the preparation of these monomethoxytrityl-protected nucleoside H-phosphonates, virtually any heterocyclic base may be utilized to prepare a particular nucleoside derivative including, but not limited to, purines, pyrimidines, or derivatives thereof. Similarly, a variety of sugar moieties may also be utilized including, but not limited to, pentoses, hexoses, ribose, deoxyribose, and derivatives thereof. In particular, typical derivatives, which are readily apparent to those skilled in the art, may include the 2'-O-ethyl, 2'-O-methyl, or the 2'-amino analogs of ribose. Other sugar groups may also be contemplated, which form part of the monomethoxytrityl-substituted nucleoside H-phosphonates of the present methods.

It is also understood that the amine protecting group on the heterocyclic bases may be varied according to the specific needs of the individual investigator. For example, diisobutyl formamidine may be used in place of the benzoyl amide group for protecting $N^6$ of adenosine (See, for example, Froehler and Matteucci in *Nucleic Acids Res.* 1983, 11(22), 8031). Methods for the attachment and removal of these amine protecting groups are well known in the art of synthetic methodology, and, therefore, the exact nature of the amine protecting group is not considered critical to the novel compositions disclosed herein. It should also be equally apparent to one skilled in the art that the novel compositions disclosed herein may be prepared with the monomethoxytrityl group present on the 3'-hydroxyl group of the sugar moiety and the H-phosphonate group on the 5'-hydroxyl end. Still other modifications and analogous compounds which may be contemplated, but which contain the essential elements of a monomethoxytrityl protecting group and an H-phosphonate functionality in a nucleoside derivative, are considered within the scope and spirit of the present invention and deemed equivalent to the novel nucleoside compositions disclosed herein.

5.2.3. Choice of Appropriate Solvents

As mentioned previously in Section 5.1, the choice of a proper solvent plays an important role in realizing the maximum benefits of the present invention. Other characteristics of the solvent may also be considered, including the ability of the solvent to solubilize to a substantial extent all the reactants and products (e.g., any salts which may cause clogging problems with a particular reactor design) involved in the preparative procedure, except, of course, the polymeric support itself. Also, the reaction solvent should not possess an acidic proton (e.g., alcohols) and should not be overly nucleophilic (e.g., aliphatic amines). Finally, the solvent of choice should not be a strong oxidant (e.g., carbon tetrachloride or carbon tertrabromide). It should be apparent, however, that alcohols, amines, or oxidizing solvents may be present in the reaction mixture, if the purpose of that particular reaction is the production of certain analogs, such as phosphate triesters, phosphoramidates, or phosphorothioates.

Consistent with the above guidelines, it has been found, for example, that the condensation solvent combination of pyridine and dichloromethane, in the presence of 2,6-lutidine, provides far superior results relative to a solvent system composed of pyridine and acetonitrile. In like fashion, great advantages have been discovered in the present invention when the oxidation to a diester is carried out in the presence of water-saturated carbon tetrachloride. The oxidation can also be performed effectively using iodine in a solvent mixture comprised mostly of aqueous pyridine instead of one favored in the prior art which consists of 90% tetrahydrofuran (See, e.g., EPA 0 219 342, page 5, line 56).

5.3. Recovery of Excess Regeant Monomer

A major portion of the cost associated with the synthesis of oligonucleotides is the expense of the 5'-protected nucleoside monomer derivatives (the cost of the controlled pore glass was also an important cost consideration in the earlier methods). These monomers are generally used in excess during the coupling cycles to ensure the participation of substantially all the available 5'-hydroxyl groups of the oligomer bound to the solid support. Thereafter, the spent reagent monomer solutions are customarily discarded in the belief that, at the very least, recovery of the unreacted monomers in a form which is useful for reuse is impractical. Quite unexpectedly, then, the present inventors have discovered a method for the large scale synthesis of oligonucleotides which not only provides very high degrees of substitution of the solid support, without sacrificing coupling efficiency and thus providing excellent yields of end product, but also allows the effective recovery of excess monomer reagents.

The process for reclaiming the unreacted monomers is made possible by a modification of the existing instrumentation to allow for the recovery of the individual monomers separately. As described above, a recovery train is installed as depicted in FIG. 2, having 5 recovery vessels, four for each of the dimethoxytrityl protected nucleoside H-phosphonates and one for the monomethoxytrityl protected nucleoside derivative which is deployed at the termination step. As usual, the system is preferably fully automated and controlled by a microprocessor. At the end of prescribed reaction times, the appropriate valves are actuated and the spent solution is directed to one of the recovery vessel labeled "U," "A," "C," "G," or "T."

In the present invention, the recovery vessels are charged with a biphasic solvent system, preferably comprising a buffered aqueous alkaline solution and a suitable water-immiscible organic solvent. A solvent mixture comprising 1M aqueous triethylammonium bicarbonate (pH 8.5) and dichloromethane is particularly preferred. In such a manner, any reactive component in the reagent solution is quenched (e.g., dehydrating agent) while the pH of the mixture is kept alkaline, thus minimizing the hydrolysis of the nucleoside protecting groups, such as those attached to the pentose sugar. The mixtures are then transferred to a large separatory funnel where the aqueous phase may be extracted repeatedly with fresh portions of a suitable organic solvent such as methylene chloride. With unexpected ease, pure intact nucleoside derivatives are then recovered by working up the combined organic layers, as described in Section 6.7, and purifying the organic residues by flash chromatography. In general, 70–90% of the amount of excess monomer is recovered by the method disclosed herein.

6. EXAMPLES

The following examples are presented herewith to better illustrate the methods and materials used in the present invention. As reasonable modifications or obvious changes will become readily apparent to those skilled in the art, based on the present disclosure, the instant examples are not to be construed as limiting the methods and materials of the invention in any manner.

6.1. General Procedures

The pivaloyl chloride (trimethylacetyl chloride) is purified by distillation at atmospheric pressure and is stored under an inert atmosphere, such as argon. The solvents (pyridine, dichloromethane, and hindered base) are dried over activated molecular sieves (3 Å). The solvents used in the coupling cycle should be as anhydrous as possible to avoid any undesirable hydrolysis reactions. The starting dimethoxytrityl protected deoxynucleoside H-phosphonates are dried by co-evaporation from anhydrous acetonitrile and, subsequently, reconstituted in anhydrous pyridine. Fragments of RNA may be prepared similarly by starting with the appropriate ribonucleoside monomers (i.e., adenosine, guanosine, inosine, cytidine, 5-methyluridine, and uridine). DNA syntheses are performed with the aid of a modified Biosearch Model 8800 DNA Synthesizer employing any swellable polymeric solid support, preferably a derivatized poly(styrene-co-(1%)divinylbenzene).

6.2. Functionalization of Solid Support

A solution of 5'-dimethoxytrityl-N2-isobutyryl-2'-deoxyguanosine-3'-succinate ester (6.15 g, 7.5 mmol) in a solvent mixture of anhydrous N,N-dimethylformamide (260 mL) and anhydrous pyridine (65 mL) is prepared under an atmosphere of argon. To this solution is added 91.5 mg (0.75 mmol) of N,N-dimethylaminopyridine, 2.84 g (22.5 mmol) of 1,3-diisopropylcarbodiimide, and 25 g (17.3 mmol) of aminomethyl poly(styrene-co-(1%)divinylbenzene). The resulting mixture is sealed under argon and shaken modestly for 4 h. The degree of substitution is determined by dimethoxytrityl cation assay as outlined in the procedure given below:

To 1 mg of the functionalized poly(styrene-co-(1%)divinylbenzene) is added 20 mL of 10% (v/v) dichloroacetic acid in dichloromethane. The resulting solution is diluted to 80 mL with 0.1M p-toluenesulfonic acid in acetonitrile. The absorption of this solution using a standard cell at 498 nm is then measured, and the degree of substitution may then be calculated using equation (1). After the desired loading is achieved, typically between 200 and 300 μmol of nucleoside $$\text{Substitution } (\mu mol/g) = A_{498} \times 14.3 \times 80 \tag{1}$$

per gram of functionalized solid support, the unfunctionalized aminomethyl groups remaining in the copolymer are "capped" with acetyl groups by the sequential addition of anhydrous pyridine (125 mL) to the reaction mixture, followed by acetic anhydride (175 mL). This mixture is, once again, sealed under argon and shaken for 1 h. Any "uncapped" amino group may be detected by placing 1 mg of the acetylated copolymer in 1 mL of a solution prepared by dissolving picryl sulfonic acid (30 mg) in 3 mL of saturated aqueous sodium borate. After the addition of a few drops of methanol, to bring down any suspended copolymer, a change in the color of the white copolymer is monitored. The presence of free amine is indicated by the observation of a yellow to an orange color; if no change is observed, the acetylation is complete. Thereafter, the functionalized and "capped" solid support is washed sequentially with fresh dichloromethane (2 ×400 mL), methanol (2×200 mL), and diethyl ether (2×200 mL). Finally, the copolymer is dried under vacuum. With the procedure described above, functionalized solid supports having nucleoside substitution values of about 150 to about 1000 μmol/g are obtained readily.

6.3. Preparation of DNA H-Phosphonate

The oligonucleotide H-phosphonate having the sequence: 5'-TCG-TCG-CTG-TCT-CCG-3', derived from a 14-mer described by Matsukura et al. in Proc. Natl. Acad. Sci. USA 1987, 84, 7706, is prepared according to the following procedure.

First, functionalized copolymer (1.0 g, substituted to a value of 253 μmol nucleoside/g), prepared by the method of Section 6.2, is placed in a reactor vessel and swollen with dichloromethane (40 mL). Conditioning is achieved by washing the solid support eight times with 10 mL portions of dichloromethane, allowing the copolymer to be in contact with the wash solvent for about two minutes for each wash (8×10 mL×2 min). Then, 3% dichloroacetic acid in dichloromethane (v/v) is introduced and purged in 11 mL portions (10×11 mL ×2.5 min) to remove the 5' protecting group of the copolymer-bound nucleoside. After the deprotection step, the solid support is subjected to a dichloromethane wash (8×10 mL×2 min), followed by an anhydrous pyridine wash (6×13 mL×2.5 min).

Following the conditioning and deprotection steps, the first coupling cycle is initiated by the addition of 6 mL of a reagent solution prepared by combining equal volumes of a 150 mM solution of 5'-dimethoxytrityl[N4-benzoyldeoxycytidine] 3'-H-phosphonate in anhydrous pyridine and 100 mM pivaloyl chloride in a solvent mixture of 2,6-lutidine/anhydrous dichloromethane (1:9, v/v, about 1.5 equiv of reagent monomer and about 1 equiv of dehydrating agent, per equiv of copolymer-bound nucleoside). After allowing the reagent solution to be in contact with the solid support for about 100 min, the spent reagent solution which still contains valuable excess deoxynucleoside H-phosphonate is recovered and set aside. The solid support is washed subsequently with anhydrous pyridine (6×13 mL×2.5 min). The preceding coupling, monomer recovery, and wash steps are then repeated once more.

Optionally, any 5'-hydroxyl groups on the copolymer bound nucleoside which remain unreacted are "capped" by the addition of 6 mL (1.5 equiv of capping monomer per equiv of copolymer-bound nucleoside) of a capping solution prepared by combining equal volumes of a 150 mM solution of ethyl H-phosphonate in anhydrous pyridine and 100 mM pivaloyl chloride in a solvent mixture of 2'6-lutidine/anhydrous dichloromethane (1:9, v/v). The capping solution is incubated with the solid support for about 100 min at ambient temperature. Afterwards, the capping solution is purged from the solid support.

Subsequent coupling cycles are initiated, up to the penultimate base, by repeating the sequence of steps outlined above beginning with the conditioning step and ending with the optional "capping" sequence, using the reagent monomers corresponding to the oligonucleotide chain described, above.

Prior to the introduction of the final base residue (i.e., T) to the 5'-end of the oligonucleotide, the solid support is conditioned, deprotected, and subjected once more to the dichloromethane and anhydrous pyridine wash steps mentioned previously. The final coupling cycle is then initiated by the addition and incubation of the a final reagent solution under the conditions described above, except that the reagent monomer is a 5'-monomethoxytritylthymidine 3'-H-phosphonate, which is prepared by the procedure described in Section 6.9, infra. As mentioned earlier, use of the monomethoxytrityl group, as opposed to the dimethoxytrityl reagent, serves at least two functions: that of distinguishing successfully prepared full length oligonucleotide sequences from the failed truncated chains and better protecting the 5'-end from the relatively harsh reaction conditions encoutered in the oxidation and cleavage steps (vide infra). The spent final reagent solution is again separated and set aside, and the residual solid support is washed with anhydrous pyridine (6×13 mL×2.5 min), as before. The final coupling cycle is then repeated once more, complete with monomer recovery and pyridine wash steps. The resulting solid support is then washed with dichloromethane (8×10 mL×2 min), followed by pyridine (6×13 mL×2.5 min).

The preceding method may be used routinely for the synthesis of a wide variety of oligonucleotides from dimers to 30-mers and, perhaps, longer chains. It should be apparent to one skilled in the art that nucleoside oligomers may be introduced at any given coupling cycle, and that based on the disclosures described herein, other modifications and related procedures may be contemplated which are considered fully within the scope and spirit of the present invention.

6.4 Oxidation of the Oligonucleotide H-Phosphonate to the Thiophosphate

The DNA H-phosphonate, prepared from the previous Section, is converted directly to the thiophosphate, preferably while the DNA is still bound to the solid support, by the addition to the reactor vessel of 16 mL of an oxidizing mixture comprised of a 2.5 wt % solution of elemental sulfur (sublimed sulfur powder available from Aldrich Chemical Company, Milwaukee, Wis., USA, Cat No. 21,523-6) in anhydrous pyridine/carbon disulfide (1:1, v/v). The contents of the reactor are mixed for about 20 min, and then the spent mixture is separated. This oxidation cycle is carried out a second, a third, and a fourth time, the last two times using 12 mL of an oxidizing solution comprising equal volumes of a 2.5 wt % solution of elemental sulfur in anhydrous pyridine/carbon disulfide (1:1, v/v) and 10% by volume diisopropylethylamine in anhydrous pyridine. Finally, the oxidized copolymer-bound oligonucleotide is washed with anhydrous pyridine (12×13 mL×2.5 min), followed by anhydrous dichloromethane (8×10 mL×2.5 min).

6.5. Oxidation of the Oligonucleotide H-Phosphonate to the Phosphodiester and the Phosphoramidate Analog The oligonucleotide H-phosphonate is oxidized, if desired, to the phosphodiester derivative by one of the following procedures:

Method A

To the solid support, obtained from the process outlined in Section 6.3, is added 16 mL of an oxidizing solvent mixture comprised of 0.1M $I_2$ in water/pyridine (2:98, v/v). The resulting mixture is agitated for about 5 min, and then the spent oxidizing solvent mixture is purged to waste. This oxidation process is repeated once with a contact time between the reactants of about 5 min and a second time with the contact time prolonged to about 30 min. Afterwards, 24 mL a second oxidizing solvent mixture comprising equal volumes of 0.1M $I_2$ in water/pyridine (2:98, v/v) and 0.1M triethyl ammonium bicarbonate in water/pyridine (1:9, v/v) is added to the solid support. After mixing the contents of the reactor for about 50 min, the spent second oxidizing solvent mixture is purged to waste and this last step repeated once more, under the same conditions. Finally, the oxidized copolymer-bound product is subjected to an anhydrous pyridine wash (12×13 mL×2.5 min), followed by anhydrous dichloromethane (8×10 mL×2.5 min).

Method B

To the solid support, obtained from the process outlined in Section 6.3, is added 25 mL of an oxidizing solvent mixture comprising a water-saturated mixture of carbon tetrachloride, triethylamine, and N-methylimidazole (18:1:1, v/v/v). The resulting mixture is agitated for 5 min, after which time the spent oxidizing solvent mixture is purged to waste. This oxidation procedure is then repeated five times. Finally, the oxidized copolymer-bound product is subjected to an anhydrous pyridine wash (12×13 mL×2.5 min), followed by anhydrous dichloromethane (8×10 mL×2.5 min).

The inventors have found that the conditions of Method B, employing a perhalogenated solvent and a suitable base, are better suited to preserving the trityl protecting group at the terminal hydroxyl end of the polymer-bound oligonucleotide. Alternatively, the oligonucleotide H-phosphonate is oxidized to the phosphoramidate analog by the following procedure:

To the solid support, obtained from the process outlined in Section 6.3, is added 18 mL of an oxidizing solvent mixture comprising 10% by volume 2-methoxyethylamine in pyridine/carbon tetrachloride (1:1, v/v). The resulting mixture is agitated for 15 min, after which time the spent oxidizing solvent mixture is purged to waste. This oxidation procedure is then repeated once. Finally, the oxidized copolymer-bound product is subjected to an anhydrous pyridine wash (12×13 mL×2.5 min), followed by anhydrous dichloromethane (8×10 mL×2.5 min).

The oligonucleotide H-phosphonates may be oxidized or converted to a number of other linkage derivatives, such as phosphoric acid triesters, dithiophosphoric acids, their corresponding esters and amidates, and others which are desirable to and which are within the skill of those knowledgeable in the art. Related oxidation procedures are described, for example, in EP Application 0 219 342 by Froehler, the complete disclosure of which is incorporated herein by reference. Thus, oligonucleotides having a variety of linkages derived from phosphoric acid, such as phosphoric acid diesters, phosphoric acid triesters, thiophosphoric acid, dithiophosphoric acid, phosphoric acid thioesters, phosphoric acid dithioesters, phosphoric acid amidates, or thiophosphoric acid amidates, are readily obtained from the methods described above.

6.6. Cleavage of the Oligonucleotide From the Copolymer Support

Once the synthesis of the oligonucleotide is complete, the DNA is cleaved from the solid support, with the concurrent removal of the base protecting groups, by the addition of a solvent mixture comprised of 1:1 (v/v) concentrated aqueous ammonium hydroxide/dioxane and incubating the resulting mixture at 45° C. for 24 h. The product oligonucleotide is washed from the solid support with N,N-dimethylformamide/water (1:1, v/v, 2×250 mL), followed by dioxane/water (1:1, v/v, 2×250 mL).

Purification is effected by reverse-phase HPLC, under the conditions described further below in Section 6.8, providing 240 mg (39 $\mu$mol, 15.4% yield) of pure product having the sequence: 5'-TCG-TCG-CTG-TCT-CCG-3'. Other oligonucleotides prepared in similar fashion include: $T_{15}$, $T_{28}$, $C_{15}$, and 5'-CTT-AGC-AGA-TAG-TGC-3', all prepared at comparable yields. Using functionalized solid supports having a nucleoside substitution value of about 200 $\mu$mol/g, pure oligonucleotides, or their associated analogs, may typically be obtained at a ratio of about 200–500 mg per gram of solid support. Conceivably, the synthesis of gram to kilogram quantities of product is limited only by the size of the reactor or reaction vessel.

6.7. Recovery of Excess Protected Nuceloside H-Phosphonate

Recovery of the excess protected nucleoside H-phosphonate is best accomplished by performing the above synthesis using the reactor schematic flow diagram illustrated in FIG. 2 and described fully in Section 5.2.1. Thus, the spent reagent monomer solution, obtained from the condensation (coupling) cycle, is directed to the appropriate recovery vessel. Preferably, each recovery vessel is about 4 L in size and charged with a 1M aqueous solution of triethylammonium bicarbonate (300 mL, pH=8.5) and dichloromethane solvent (300 mL). The resulting recovery solution is then placed and shaken in a separatory funnel. The organic phase is then allowed to separate, recovered, and dried over sodium sulfate. The volatile components of the dried solution are then removed by evaporation, and the residual H-phosphonate monomer is purified by flash chromatography (silica gel, 1% triethylamine in methylene chloride as eluent with a step gradient from 0–10% methanol). Excess monomers recovered and purified in this manner are suitable for use in the synthetic methods delineated above.

6.8. HPLC Purification of Monomethoxytrityl Protected Oligonucleotide; Detrylation and Further Work Up A crude sample containing approximately 250 $\mu$mol of synthetic oligonucleotide, prepared by the methods described above, and dissolved initially in a solvent mixture comprised of 1:1 (v/v) dioxane/aqueous ammonium hydroxide (5 mL), N.N-dimethylformamide (95 mL), and water (95 mL) is diluted to a final volume of 1 liter with a 50 mM aqueous solution of triethylammonium phosphate (TEAP, pH 6.0). This dilute oligonucleotide solution is then loaded, at a flow rate of 50 mL/min, on a Septech A/E 25 cm×5 cm i.d. column packed with Hamilton PRP-1 (polystyrene stationary phase, 12–20$\mu$), which had previously been conditioned with 3 liters of a buffer solution comprised of 5% by volume of acetonitrile in 50 mM TEAP (Buffer A, pH 6.0) at a flow rate of 100 mL/min. After the completion of the sample loading, the flow rate is increased and Buffer A is pumped through the column until a baseline is reestablished. At that point, a 45 min linear gradient to 100% of Buffer B (75% by volume acetonitrile in 50 mM TEAP, pH 8.0) is initiated. Approximately 300 mL of the fraction eluting at a retention time of 17–22 min is then collected.

The collected fractions are allowed to evaporate to near dryness under reduced pressure. Detritylation is accomplished by the addition of 80% acetic acid (150–300 mL) to the residual thick gum. The resulting solution is mixed thoroughly for about 2–4 h and then filtered through a 5$\mu$ membrane filter to remove the liberated monomethoxytrityl group. The filtrates are combined, concentrated under vacuum, taken up in about 200 mL of aqueous 0.5M $Na_2HPO_4$, and loaded on the polystyrene column at a flow rate of 100 mL/min. After the loading is completed, the column is washed with distilled and deionized water at a flow rate of 100 mL/min until the conductivity of the effluent is less than or equal to about 15 $\mu$s, indicating the substantial removal of any salts which may have been present in the detritylated sample. The oligonucleotide is eluted using a 20 min linear gradient to 75% acetonitrile. The desired desalted product is collected with the fractions eluting at around 5–7 min after initiation of the linear acetonitrile gradient. After the acetonitrile is removed by evaporation under reduced pressure, the residue is lyophilized and, finally, relyophilized. About 240 mg of pure oligonucleotide is thus obtained.

6.9. Preparation of Monomethoxytritylnucleoside H-Phosphonates

The following general procedure is used to prepare a whole host of monomethoxytrityl-protected nucleoside H-phosphonates. The procedure is illustrated for the case of 5'-monomethoxytritylthymine 3'-H-phosphonate but it should be understood that any desired nucleoside may be used as starting material. Also, by employing a suitable initial protecting group for the 5'-position, the monomethoxytrityl group may be placed on the 3'-position of the sugar moiety.

Thymidine (4.8 g, 20 mmol) is dried by co-evaporation from two 100-mL portions of pyridine. The residue from the second co-evaporation is then taken up in 100 mL of dry pyridine. To this pyridine solution is added with stirring N,N-dimethylaminopyridine (0.122 g, 1 mmol) and methoxytrityl chloride (6.8 g, 22 mmol). After 24 h of stirring at room temperature, the reaction is quenched with the addition of methanol (1 mL), and the volume of the reaction mixture is reduced to about 25 mL under reduced pressure. Methylene chloride (200 mL) is then added to dilute the mixture which is transferred to a separatory funnel, washed with 5% aqueous sodium bicarbonate (2×200 mL), and dried over sodium sulfate. The volatile components of the mixture are then removed under reduced pressure, leaving a foam.

The crude 5'-monomethoxytritylthymidine is taken up in 50 mL of pyridine. The solvent is then removed under reduced pressure, and the residue is redissolved in 75 mL of a solvent mixture comprising methylene chloride/pyridine (2:1, v/v). The resulting solution is then added, with stirring and under an inert atmosphere, to 50 mL of a 0.6M solution of salicylchloro-phosphite (Cf. Marugg et al. *Tetrahedron Lett.* 1986, 27(23), 2661) in methylene chloride/pyridine (1 5:1, v/v). After 30 min of stirring at room temperature, the reaction mixture is poured into a 1M aqueous solution of triethylammonium bicarbonate (TEAB, 350 mL). The aqueous phase is then separated and extracted with fresh methylene chloride (300 mL). The combined organic layers are then washed with 300 mL of the aqueous 1M TEAB, and the water phase is again separated and extracted with fresh methylene chloride (200 mL). The organic phases are combined, dried over sodium sulfate, and concentrated under vacuum. The crude product mixture is purified by column chromatography on silica gel, using a 1% triethylamine in methylene chloride eluent with a methanol step gradient (0 to 10%, increased 1% after each column volume of solvent introduced). The fractions containing the desired product are then pooled, concentrated, taken up in methylene chloride (200 mL), and washed with a 1M aqueous solution of 1,8-diazabicyclo[5.4.0]undec-7-ene (DBU) bicarbonate (200 mL). Following removal of the volatile components of the solution, 11.3 g (85%) of the product H-phosphonate is obtained, as the DBU salt.

1H NMR (CDCl$_3$): δ 7.95 (s, 0.5 H), 7.60 (s, 1 H), 7.45–7.35 (m, 4 H), 7.30–7.20 (m, 9 H), 6.82 (d, 2 H), 6.45 (m, 1 H), 5.95 (s, 0.5 H), 5.05 (m, 1 H), 4.30 (m, 1 H), 3.80 (s, 3 H), 3.45 (m, 8 H). 2.85 (m, 2 H), 2.65 (m, 1 H), 2.40 (m, 2 H), 1.75 (m, 7 H), and 1.30 (s, 3 H) in ppm downfield from tetramethylsilane; $^{31}$P NMR (CDCl$_3$) δ -3.32 ($J_{(P-H)}$=611 Hz, $J_{(P-OCH)}$=8.5 Hz) in ppm downfield from external 5% phosphoric acid in D$_2$O.

What is claimed is:

1. A nucleoside compound comprising a heterocyclic base and a sugar, which sugar has at least two hydroxyl ends one of which ends is blocked by a monomethoxytrityl group and the other end bearing a H-phosphonate group.

2. The 5'-monomethoxytritylnucleoside 3'-H-phosphonate of claim 1 in which said heterocyclic base is selected from the group consisting of purine, pyrimidine, and derivatives thereof.

3. The nucleoside compound 3'-H-phosphonate of claim 1 in which said heterocyclic base is selected from the group consisting of thymine, adenine, cytosine, guanine, uracil, and derivatives thereof.

4. The nucleoside compound of claim 1 in which said heterocyclic base further comprises amino protecting group.

5. The nucleoside compound of claim 1 in which said sugar is selected from the group consisting of pentose, hexose, and derivatives thereof.

6. The nucleoside compound of claim 1 in which said sugar is a pentose selected from the group consisting of ribose, deoxyribose, and derivatives thereof.

7. The nucleoside compound of claim 1 in which said sugar has a 5'-hydroxyl end and a 3'-hydroxyl end.

8. The nucleoside compound of claim 7 in which said monomethoxytrityl group is present at said 5'-hydroxyl end and said H-phosphonate group is present at said 3'-hydroxyl end.

9. A nucleoside compound which is 5'-monomethoxytritylthymidine 3'-H-phosphonate.

10. A 5'-monomethoxytritylnucleoside 3'-H-phosphonate which is 5'-monomethoxytrityl-N$^6$benzoyldeoxyadenosine 3'-H-phosphonate.

11. A 5'-monomethoxytritylnucleoside 3'-H-phosphonate which is 5'-monomethoxytrityl-N$^4$-benzoyldeoxycytidine 3'-H-phosphonate.

12. A 5'-monomethoxytritylnucleoside 3'-phosphonate which is 5'-monomethoxytrityl-N$^2$-isobutyryldeoxyguanosine 3'-H-phosphonate.

13. A 5'-monomethoxytritylnucleoside 3'-H-phosphonate which is 5'-monomethoxytrityl-N$^4$-benzoyldeoxy-5-methylcytidine 3'-H-phosphonate.

14. A 5'-monomethoxytritylnucleoside 3'-H-phosphonate which is 5'-monomethoxytrityl-5-bromouridine 3'-H-phosphonate.

* * * * *